(12) United States Patent
Grim et al.

(10) Patent No.: US 7,465,281 B2
(45) Date of Patent: Dec. 16, 2008

(54) VERSATILE HARDENABLE CAST OR SUPPORT

(75) Inventors: Tracy E. Grim, Tulsa, OK (US); Wendy J. Henderson, Ventura, CA (US); Kelly M. Long, Woodland Hills, CA (US); Joseph M. Iglesias, Thousand Oaks, CA (US); Michael Campos, El Rio, CA (US)

(73) Assignee: Ossur, hf, Reykjavik (IS)

( * ) Notice: Subject to any disclaimer, the term of this patent is extended or adjusted under 35 U.S.C. 154(b) by 0 days.

(21) Appl. No.: 10/419,307

(22) Filed: Apr. 18, 2003

(65) Prior Publication Data

US 2004/0210177 A1  Oct. 21, 2004

(51) Int. Cl.
*A61F 5/00* (2006.01)

(52) U.S. Cl. .............. 602/5; 602/16; 602/20; 602/21; 602/23; 602/27

(58) Field of Classification Search .......... 602/5–9, 602/12, 16, 20–21, 23, 27, 41, 60–62, 64, 602/65; 128/880, 878, 882; 2/16; 424/433, 424/445

See application file for complete search history.

(56) References Cited

U.S. PATENT DOCUMENTS

| | | | | |
|---|---|---|---|---|
| 3,656,475 A | * | 4/1972 | Hanrahan, Jr. | 602/8 |
| 4,331,134 A | * | 5/1982 | Brooks et al. | 602/8 |
| 4,683,877 A | | 8/1987 | Ersfeld et al. | |
| 4,798,200 A | * | 1/1989 | Warthen et al. | 602/6 |
| 4,852,557 A | | 8/1989 | Grim | |
| 5,195,944 A | * | 3/1993 | Schlogel | 602/5 |
| 5,195,945 A | * | 3/1993 | Sandvig et al. | 602/8 |
| 5,228,164 A | * | 7/1993 | Graf et al. | 12/133 R |
| 5,732,713 A | * | 3/1998 | Duback et al. | 128/846 |
| 5,842,475 A | | 12/1998 | Duback et al. | |
| 5,868,693 A | * | 2/1999 | Duback et al. | 602/27 |
| 5,931,798 A | * | 8/1999 | Green et al. | 602/6 |
| 6,022,331 A | * | 2/2000 | Darcey | 602/12 |
| 6,039,706 A | * | 3/2000 | Bolla et al. | 602/5 |
| 6,139,513 A | * | 10/2000 | Grim et al. | 602/6 |
| 6,145,134 A | * | 11/2000 | Davis et al. | 2/463 |
| 6,269,485 B1 | * | 8/2001 | Foreman | 602/8 |
| 6,595,937 B1 | * | 7/2003 | Moon et al. | 602/5 |
| 2004/0077980 A1 | * | 4/2004 | Stess et al. | 602/6 |

* cited by examiner

*Primary Examiner*—Patricia Bianco
*Assistant Examiner*—James M Robinson
(74) *Attorney, Agent, or Firm*—Bacon & Thomas, PLLC

(57) ABSTRACT

A cast or support for use in limiting movement of the anatomy to promote healing of an injured body part includes initially flexible and subsequently rigid double-knit material, or other casting blanks. There is a water-hardenable material impregnated into the casting blank. Certain areas of the blank have significantly reduced or no hardenable material. This construction may provide at least one hinge line which extends substantially across the double-knit material or other casting blank where the upper and lower layers are held in engagement with each other. The cast or support may be folded open along the hinge line to permit washing, inspection, or treatment of the portion of the anatomy to which the cast or support is applied or as one step in the preparation of a mold of a portion of the anatomy. More than one hinge line may be provided. Overlapping edges of the blank may also be of reduced thickness and with reduced hardening material to provide a smooth overlap to secure the cast or support in place.

18 Claims, 10 Drawing Sheets

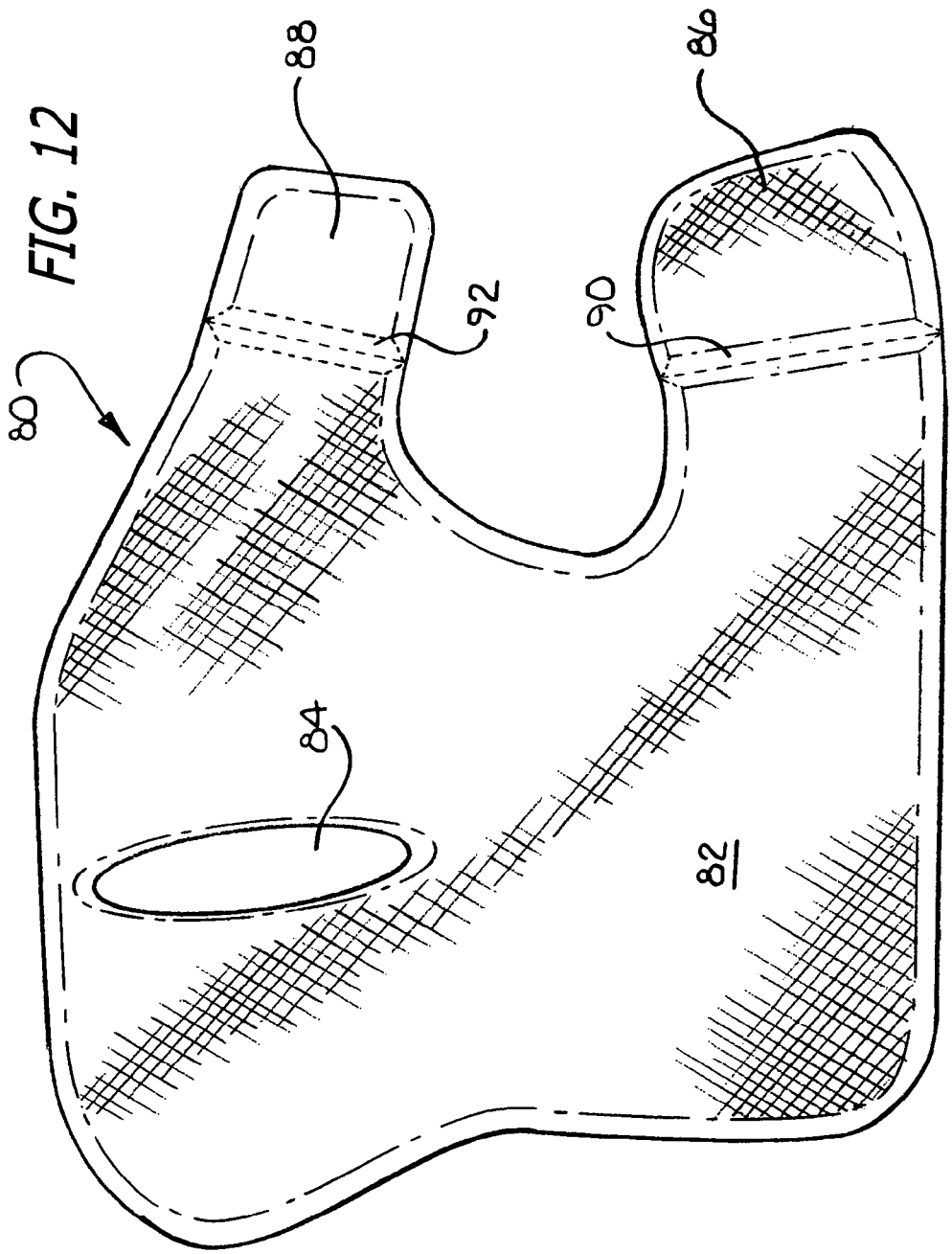

VERSATILE HARDENABLE CAST OR SUPPORT

BACKGROUND OF THE INVENTION

This invention relates to a cast or support useful for orthopedic devices, particularly a support for a portion of the human anatomy. More specifically, the invention relates to providing a support configuration for use with parts of the body which need to be relatively immobilized, and which should be accessed periodically for inspection, washing or the like, and to other related orthopedic constructions.

Treatment of injuries, such as bone fractures, often involves immobilization of portions of the body. Such immobilization can be provided by different casting materials, for example, woven or knitted fabrics impregnated with water-hardenable material such as urethane or Plaster of Paris. Since casts remain on the body for long periods of time, there can often be considerable discomfort and trauma to the patient in the regions underlying the cast. There is a need to provide an easy system for providing access to the immobilized body part for inspection and washing of the anatomy, for instance.

This invention in one important aspect is directed to providing a hardenable, removable support configuration which increases patient comfort and allows access to the anatomy for washing, changing dressings, X-raying, doctor evaluation, or the like.

SUMMARY OF THE INVENTION

According to one specific illustrative embodiment of the invention, there is provided a versatile water-hardenable cast or support which comprises a double-knit material shaped to fit a portion of the human anatomy. The double-knit material is formed of an upper layer of woven or knit material and a lower layer of woven or knit material separated at a predetermined distance by a central open-work matrix of filaments or yarns extending back and forth between the upper and lower fabric layers. This type of material is referred to from time to time in the present specification and claims as spacer material. A water hardenable material is impregnated into said double-knit type material, and there is at least one hinge line extending across the double-knit type material where the upper and lower layers are held in engagement with each other. The cast or support may be folded open along the hinge line to permit inspection or washing of the underlying portion of the anatomy, changing of a dressing or padding, or permitting the underlying area to breathe and be exposed to air. The ability to open and reclose the support can also be useful in making of molds of portions of the anatomy.

In addition, a hinge line is useful in a cast which extends around an injured limb of the patient. In the event of swelling or other need for access, the physician can saw the length of the cast on the opposite side from the hinge line, and open the cast fully for inspection, or slightly, to accommodate swelling, while still providing the desired immobilization.

There are a number of methods for creating a hinge line in an orthopedic cast or support. A first method of forming a hinge line can be accomplished in a material of thickness by disrupting the structural integrity of the fabric in this area. The spaced apart layers of the double-knit material create an I-beam type structure and, in cooperation with the resin system, provide the strength of the orthopaedic device. By engaging the top and bottom layers, the structural strength is greatly reduced in these localized areas. This compressed area can be created by sewing, ultrasonically welding, concurrent heat and pressure or any other method that will effectively hold the layers together. Other than compressing the material, it is possible to form a hinge by sewing or attaching two separate double-knit blank members directly together to form the appropriate hinge. This method of creating a hinge can be accomplished with any material of thickness such as the above mentioned double-knit material, a foam laminate, or any other material which gains strength by using spaced apart layers in combination with an inner core.

In addition to providing hinge lines, reduced thickness areas can be created around the edges of the blank to provide a smooth overlap and secure lamination of the cast blank edges together thereby securing the cast or support in place.

A second method of creating a hinge line in an orthopedic cast or support is by limiting or eliminating the amount of resin allowed in the hinge area. This method can be successful with any type of material used for the casting blank such as, double-knit material, foam laminate, multiple layers of a single-knit material, etc. Limiting resin impregnation in specific areas may be accomplished in a variety of ways such as by blocking the hinge line from resin impregnation by clamping across the blank during impregnation. Other methods to reduce the amount of resin in selected areas include impregnating the casting material with another softer, flexible material limiting or blocking the hardenable resin in this area.

In addition, a hinge line may be established by creating a weakened zone across the casting blank using a material of lesser strength in this area. This can be accomplished by inserting a separate single layer material into the casting blank in the area where reduced strength is desired. When utilizing a double-knit type fabric, it is possible to construct a varying thickness casting blank during the initial knitting of the fabric with a single-layer knit structure in the area intended to be a hinge and a double-layer knit structure in the remainder of the blank where more strength is needed.

In other embodiments of the invention, there can be more than one hinge per cast or support and/or the hinge lines do not need to be longitudinal with respect to the cast or support. Hinge lines can also be diagonal, transverse, or a combination of the two with respect to the cast or support.

It may be noted that, instead of using double-knit material, other casting materials such as an open cell foam, or casting blanks having a significant thickness, could be employed in the implementation of the invention.

For ease in hinging open and closing the cast or support, the hinge lines should be substantially straight, although very slight departures from straight hinge lines are acceptable and provide both a closed stable configuration and an open stable configuration. In a method of employing the hinge, the method comprises forming a cast or support blank with a hinge line extending across said blank, impregnating the blank with hardenable material; activating said hardenable material; applying the cast or support to a portion of the anatomy and permitting the hardenable material to harden; opening the cast or support at the hinge line and removing it from the anatomy; closing the cast or support; and filling the cast or support with a hardenable material to form a substantial replica of the portion of the anatomy.

Other objects, features and advantages of the invention will become apparent from a consideration of the following detailed description and the accompanying drawings.

BRIEF DESCRIPTION OF THE DRAWINGS

FIG. 12 shows a hardenable blank for supporting the forearm and wrist, including strap base members which are hingedly coupled to the main portion of the blank;

DETAILED DESCRIPTION OF THE PREFERRED EMBODIMENTS

Figure 1:
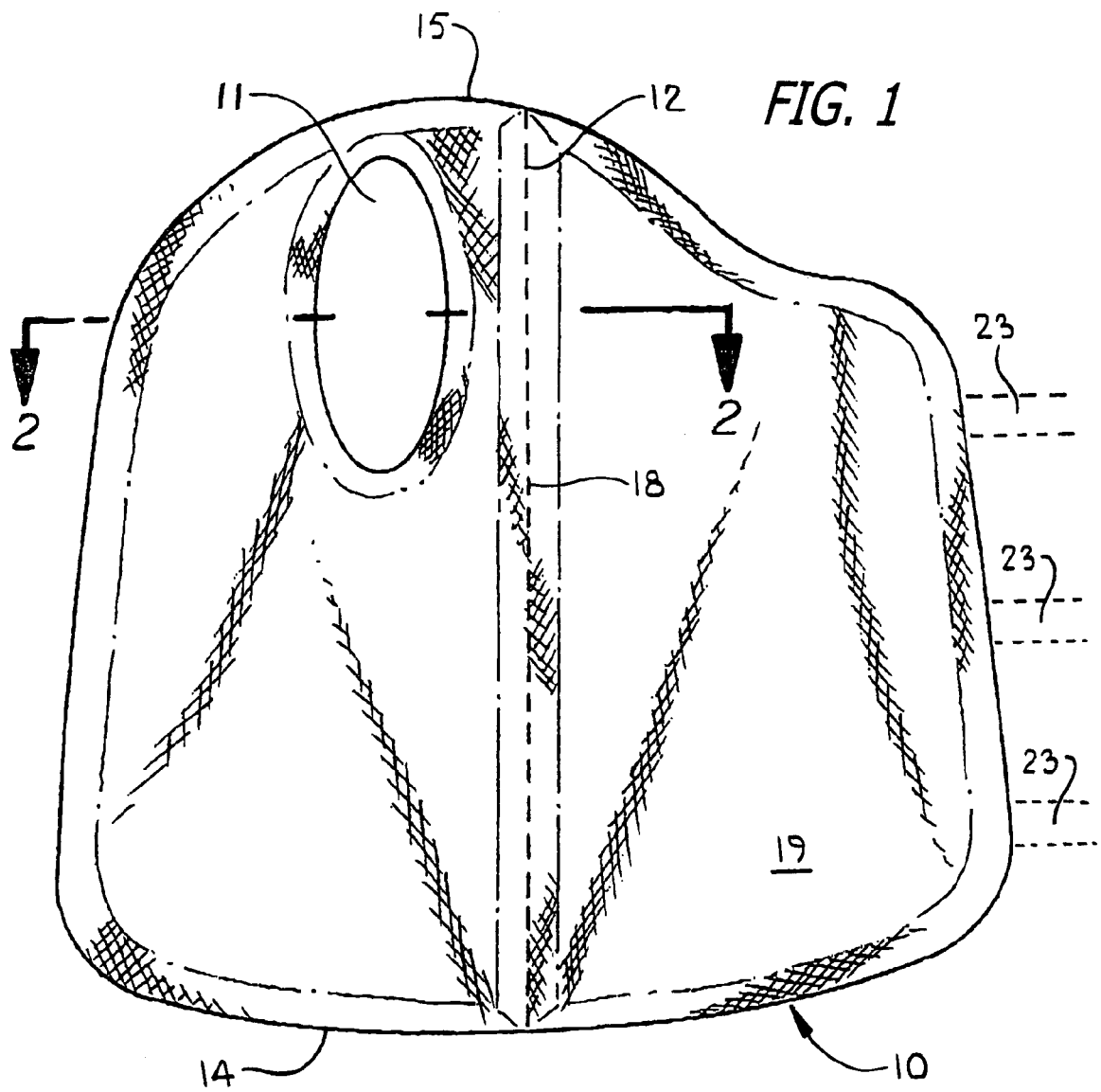
FIG. 1 is a plan view showing the flat double-knit material as used to support a forearm, with a hole to receive a thumb, and a hinge line extending across the double-knit material.

The invention is now further described with reference to the accompanying drawings, which show by way of illustration specific embodiments in which the invention may be practiced. It is to be understood that other embodiments may be utilized and structural and functional changes may be made without departing from the scope of the present invention.

Referring more particularly to FIGS. 1 through 5 and FIGS. 7 and 8, a cast for a hand or wrist to promote the healing of an injury comprises a material 10, which is initially flexible and can be formed of a woven or knitted material, and may be impregnated with a hardenable material such as a water curable polyurethane. When activated, this material can form a suitably rigid structure to relatively immobilize a portion of the body such as the hand, wrist or arm 22. As shown, the material 10 includes an aperture 11 for receiving the thumb 16 of the patient (see FIG. 3)

In the preferred embodiment, material 10 may be formed of double-knit type fabric with an outer woven or knit fabric layer, and an inner woven or knit fabric layer, with these two layers being spaced apart and secured together with a matrix of filaments which extend between and which are integrally woven or knit into the outer and inner layers 19 and 20. Both the matrix of filaments and the two surface layers may be impregnated with an activatable material. In another embodiment, the material 10 can be formed of three component elements. An element or surface 19 provides a first knit surface, a second element or surface 20 provides another knit surface, and between them there is a cellular material 21 which absorbs a water hardenable material to become rigid and thereby form the cast or support around the body part to be immobilized. In addition to the cellular material, both knit surfaces 19 and 20 may also be impregnated with a hardenable material to add to the rigidity of the cast or support.

The material 10 can readily hold a chemical constituent which is treatable to change from a flexible state to a rigid state. As such, the material 10 includes at least three layers: a first boundary layer, a second boundary layer, and a cellular layer or matrix of filaments between the first and second boundary layers. The assembly is impregnated with a polyurethane which is activated with water to form a rigid construction.

Figure 2:
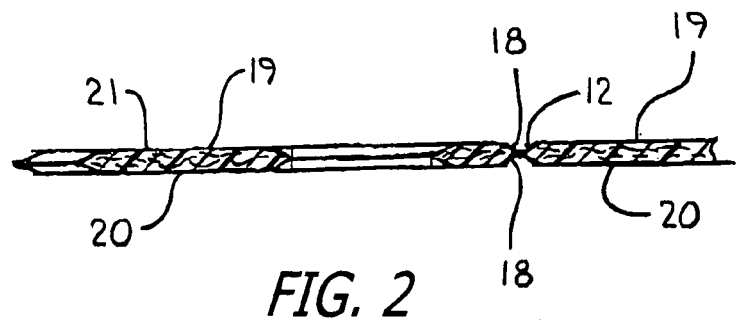
FIG. 2 is a partial cross-sectional view of FIG. 1, taken along line 2-2 of FIG. 1.

As shown in FIG. 1 there is a hinge line 12 which extends from one edge 14 of the blank material 10 to an opposite edge 15 of the casting blank 10. As shown in FIG. 2, the first element or surface 19 is compressed towards the second surface 20 at the location of the hinge 12 so that ideally a thin zone is provided thereto to create the hinge area. A V-shaped formation 18 is formed where the material 10 is compressed along the line 12. As a specific example, this compression may be accomplished by stitching along line 12, thus bringing the upper and lower layers 19 and 20 together and compressing the central section 21, so that very little hardenable material is present along the intended hinge line 12 and also reducing the structural integrity of the double-knit fabric. This facilitates hinging action as required to open or close the support.

Figure 4:
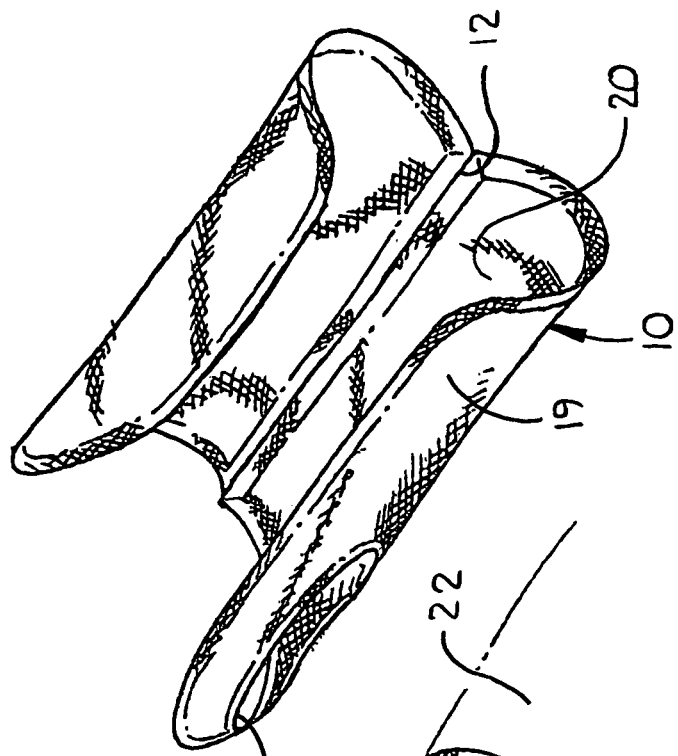
FIG. 4 is a perspective view of the cast in an open position.
Figure 3:
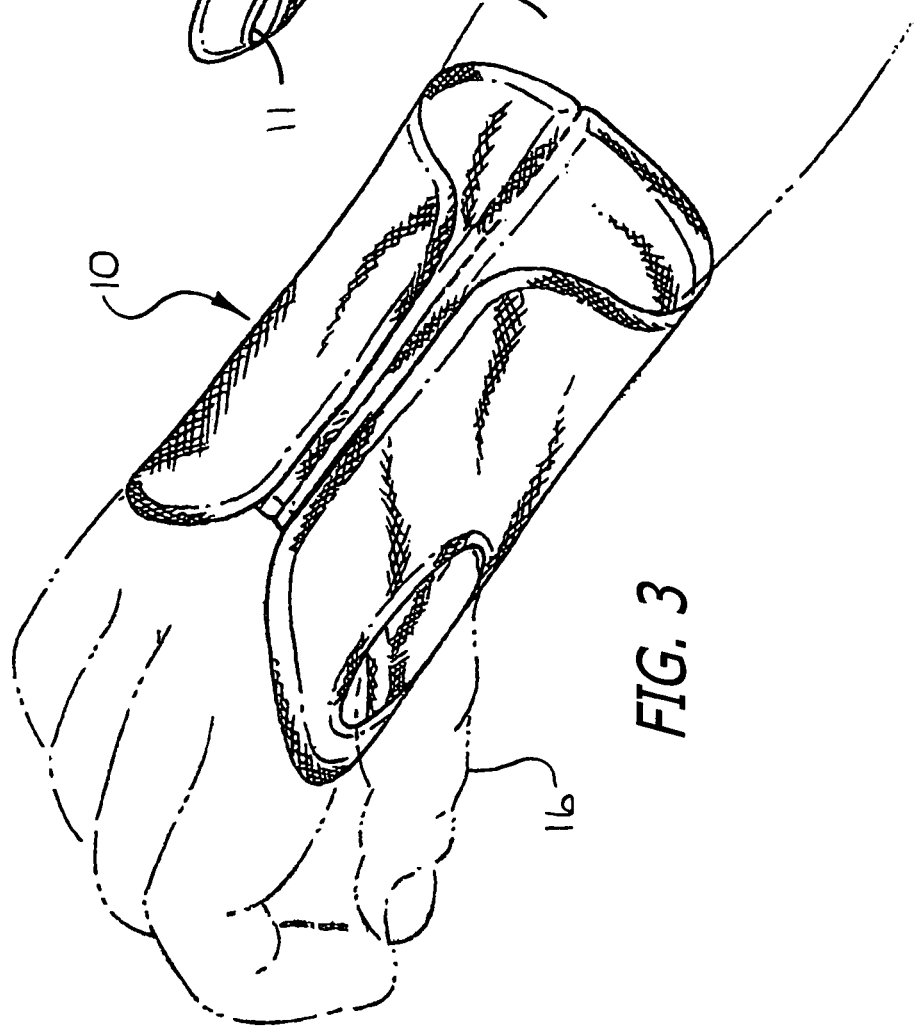
FIG. 3 is a perspective view of the cast in a closed position.

In use, a thumb 16 (see FIG. 3) is pushed through the aperture 11 and the material 10 is wrapped around the wrist and lower portion of the hand as necessary to provide suitable immobilization of the forearm and wrist of the patient. The hardenable material is activated to initiate hardening of the casting blank so as to effectively immobilize that portion of the body. This would normally be accomplished by dipping the blank 10 into water prior to application, but in some cases the casting blank could be applied first followed by the water application, or the injured limb or part of the body could be dipped into water following application of the casting blank. When it is necessary or desired, the support may be opened about hinge 12 as shown in FIG. 4. The anatomical part 22 can then be washed or otherwise treated.

An additional advantage of being able to easily open and close a support or cast involves taking a mold of a portion of the anatomy. The support 10 is activated and molded to the anatomy. Once hardened, the support is opened along the provided hinge line. The anatomy is easily removed from the support which can then be returned to its previous shape and used to make an exact mold of the anatomy. Incidentally, the taking of a mold of a portion of the anatomy is one step of the fabrication of custom orthopaedic equipment.

To hold the support 10 around the arm, suitable strapping or the like can be provided transversely to maintain proper immobilization. Releasable straps, as indicated at reference numeral 23 in FIG. 1, may be employed to hold the cast closed or to release and permit hinging open. Such strapping configurations are well known in the art, and reference is made to U.S. Pat. No. 6,007,505 assigned to the assignee of the present application wherein such straps are shown. The contents of the patent are hereby incorporated by reference into this application. Alternatively, the edges of the casting blank 10 may be provided with overlapping Velcro® type hook and loop material to hold the casting blank in place. It is also possible for the edge of the casting blank to overlap and be secured by lamination of the layers, as indicated hereinbelow in connection with FIGS. 9, 10 and 11. Once the cast is opened along the hinge lines it can be reapplied and held closed with strapping or functionally equivalent arrangements, as discussed above.

Figure 5:
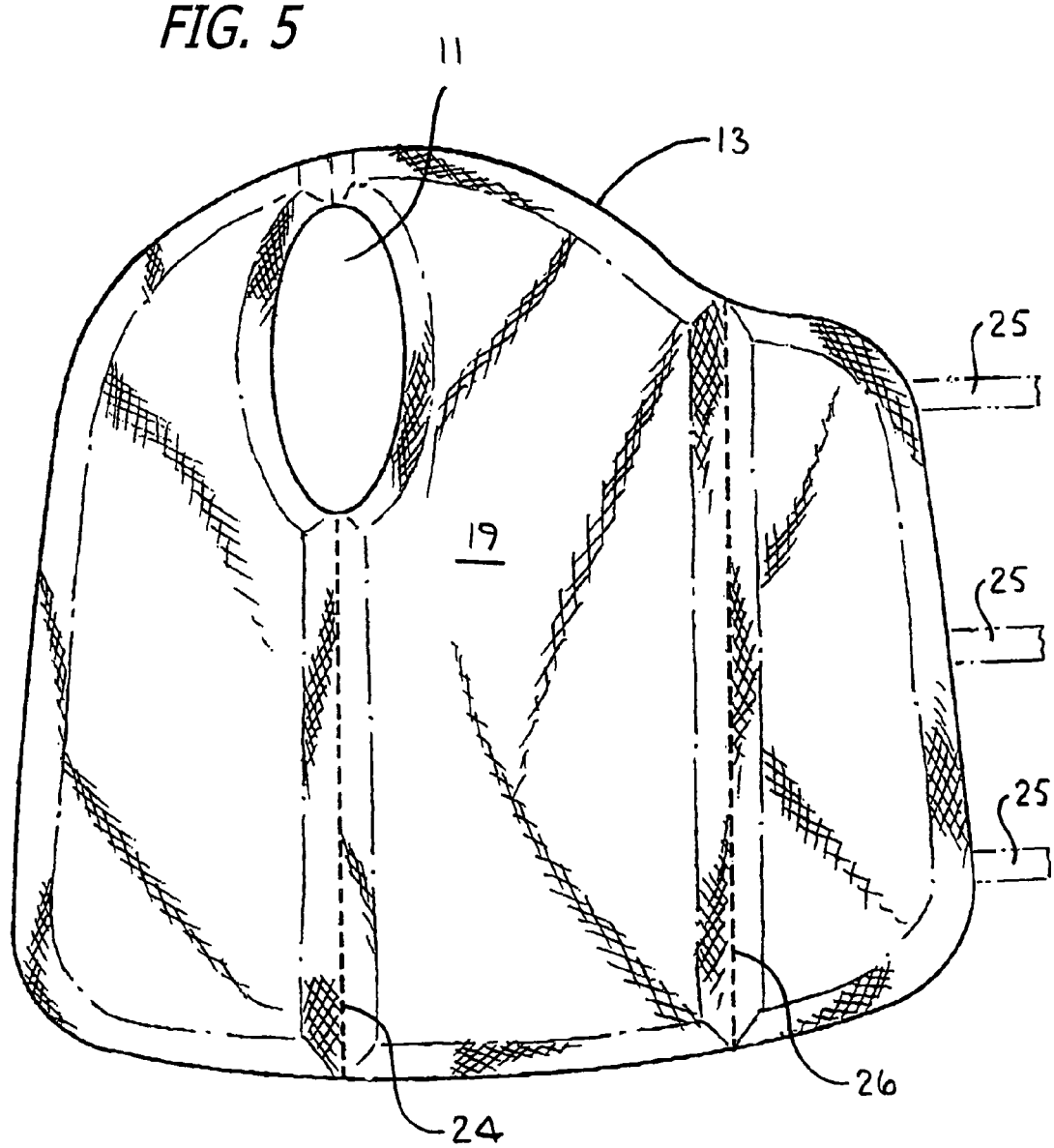
FIG. 5 is a plan view showing the flat material as used to support a forearm, with a thumb-hole to receive a thumb, and two hinge lines shown extending across the double-knit material.
Figure 7:
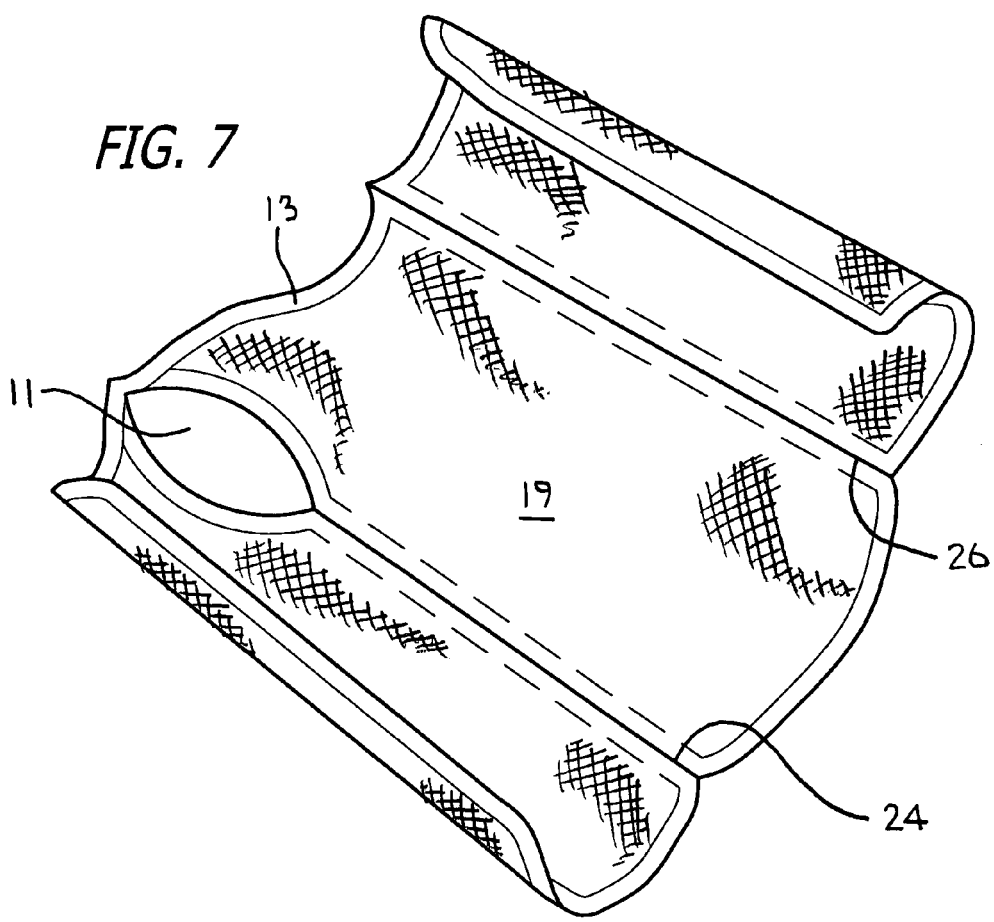
FIG. 7 is a perspective view of a support in an open position with two hinge lines shown extending across the casting material.

FIG. 5 shows a blank 13 similar to that shown in FIG. 1. In the configuration of FIG. 5, however, there are two hinge lines 24 and 26. The configuration shown here permits the support to be opened at one or both places as is necessary to obtain access to the body part. FIG. 7 shows this same configuration after it has been conformed to the anatomy and opened along the two hinge lines 24 and 26. In cases where a cast or support needs to be slightly loosened to allow for swelling, either one or both of these hinges can be partially opened. In FIG. 5, straps 25 are provided to permit easy opening and closing of the cast.

Figure 6:
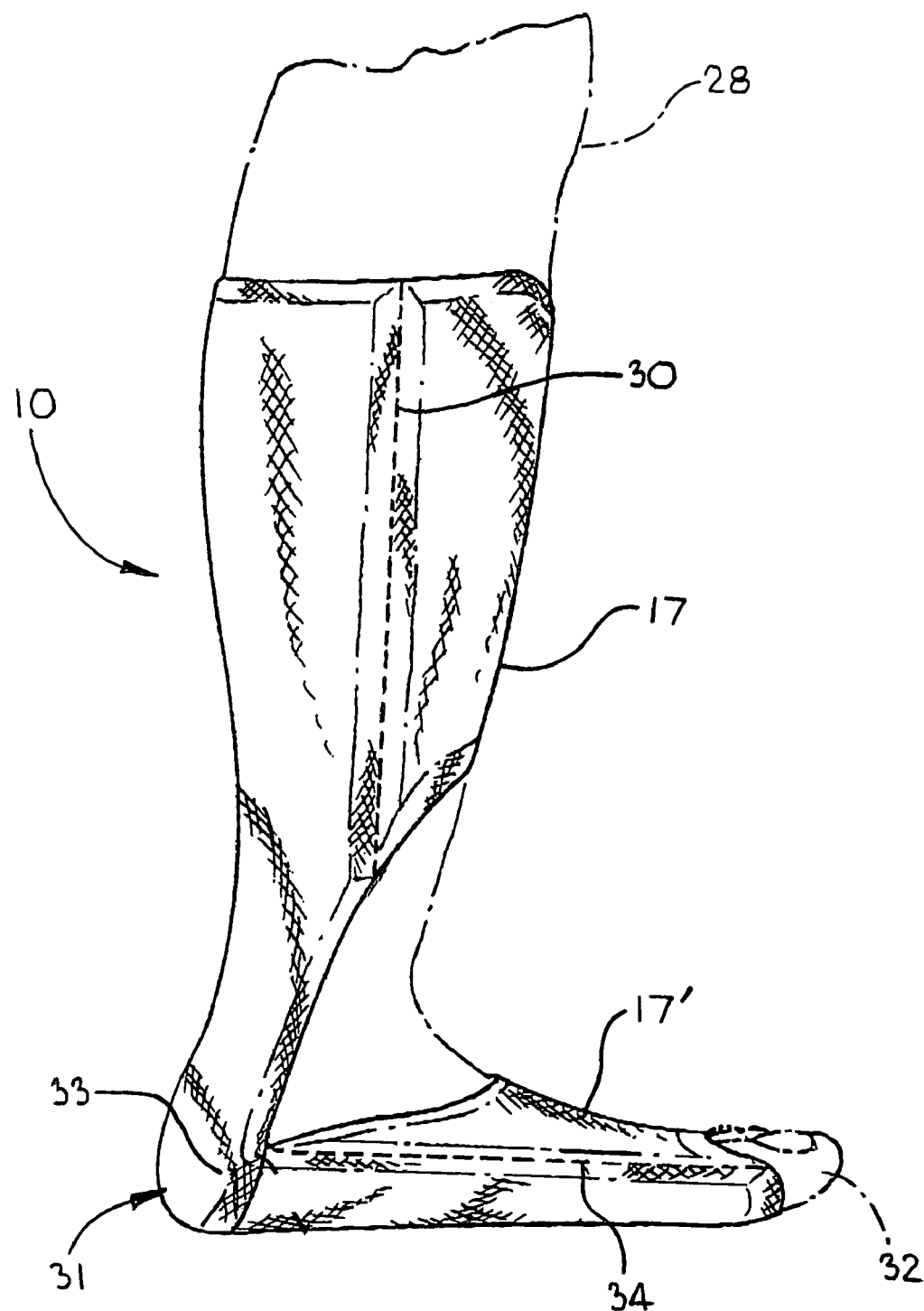
FIG. 6 is a side view of the cast in a closed position over a leg and foot and showing the hinge lines.

In FIG. 6 there is shown a cast or support for location about the lower leg 28 comprising a material 10 which is impregnated with an activatable material. The support has one hinge 30 located in a manner to extend longitudinally up the leg, and has another hinge line (not shown) on the other side of the lower leg directly opposite the hinge line 30. The support also extends down and around the foot, and this portion of the support is designated by the reference numeral 17'. The cast is initially a flat blank, with the area 17 extending partially around the calf of the leg in both directions, and is cut to be relatively thin in the area 31 where it is intended to extend around the heel of the user. It then broadens out to the area 17' where flaps extend up over the top of the foot. Note also that there is an area of overlap 33 where the cast portion 17 overlaps the adjacent areas of the cast portion 17' to form a rigid overall lower leg and foot support. It may be noted that the hinge line 34 extends transversely and in line with the general orientation of the foot 32 along the cast portion 17'. Another opposite hinge line 34 may be provided in the second flap (not shown) which extends over the foot from the rear in FIG. 6. Opening of the cast at one or more of the multiple hinges allows for removal of the cast so that washing or treatment of the lower leg is possible. Again, suitable strapping or the like can be provided to return the cast to its original configuration and maintain proper immobilization once the cast has been opened and reapplied. The shape of the support is, of course, different from the support as illustrated in FIGS. 1-5, with each cast uniquely shaped for the part of the anatomy requiring support.

Figure 8:
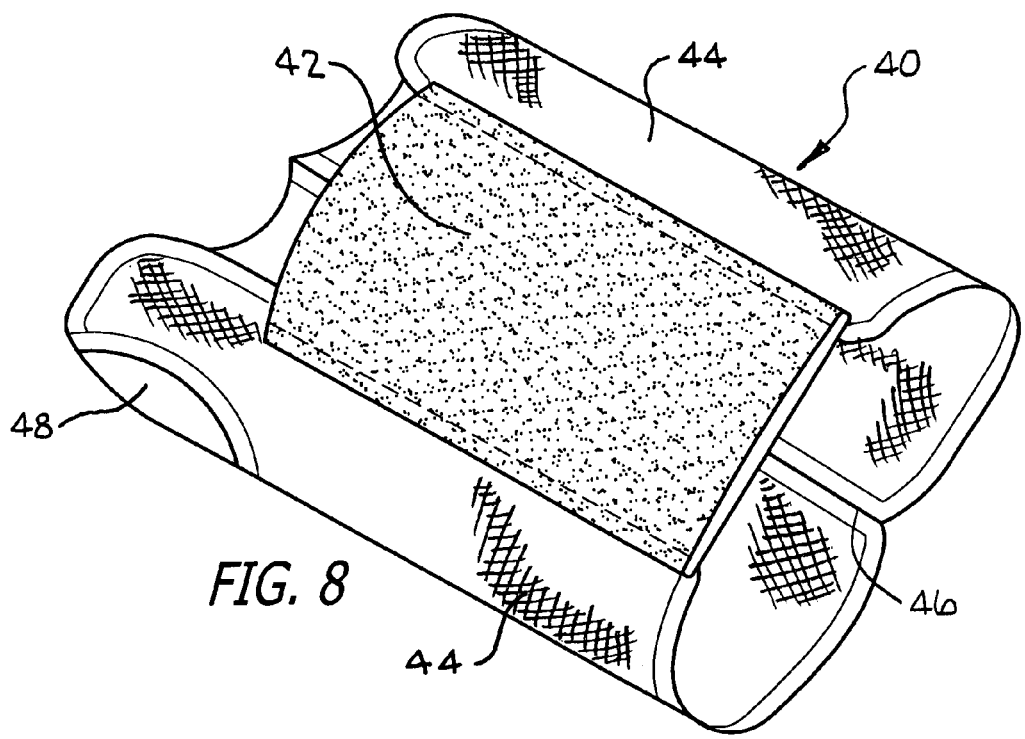
FIG. 8 is a perspective view of a casting blank with stockinette attached to hold the opposing edges close to one another for easy application.

A further embodiment 40 is shown in FIG. 8 where stockinette type material 42 is attached to both opposing edges of the casting blank 44, which is provided with a hinge line 46 of the type described hereinabove. This type of configuration is used to hold the support in a three-dimensional form prior to application for more intuitive and easier application. The stockinette material is a thin, stretchable loosely knit or woven material, and is preferably not impregnated with the water hardenable material. In use, the casting blank 44 with attached stockinette material 42 is removed from its packaging and activated. Preferably, the casting blank 44 has pre-attached padding and covering materials surrounding it to prevent resin from getting on the stockinette or other unwanted items. The support is slid over the hand and arm with the thumb pushed through aperture 48 in this specific example. The product is then molded to conform to the anatomy and hardens to properly immobilize the injured body part. To rigidly hold the support to the anatomy, straps, overlapping laminating edges or other arrangements as described herein may be employed.

Figure 9:
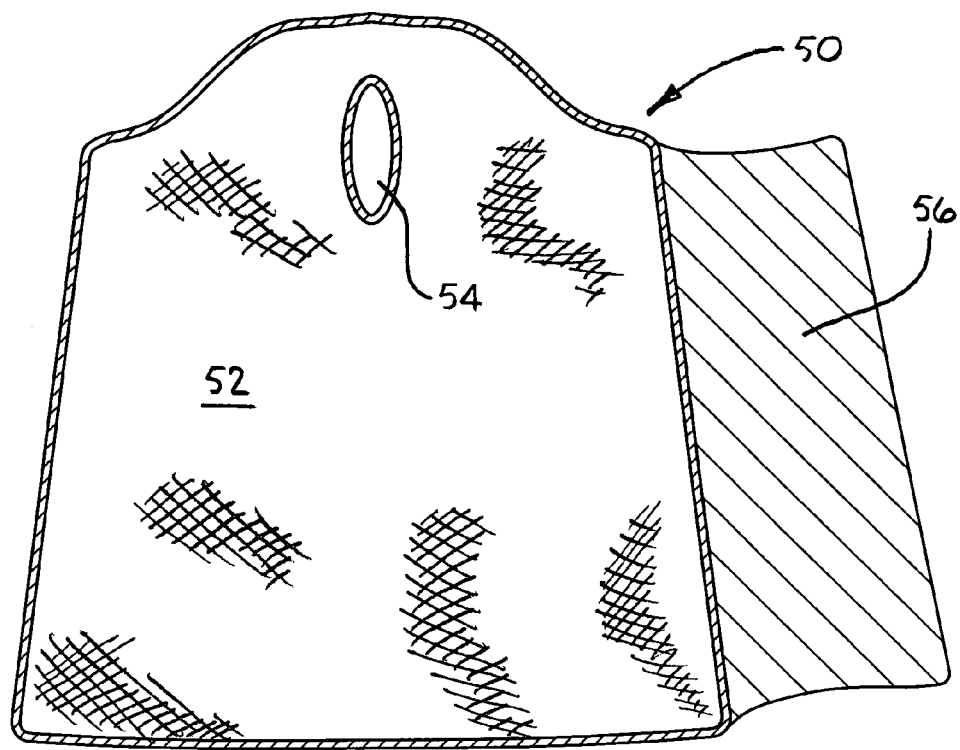
FIG. 9 is a plan view of a casting blank with a broad area of reduced thickness at one edge for holding the cast in place.

FIG. 9 shows an embodiment of the invention in which a cast or support 50 may be formed of double-knit material 52 impregnated with water hardenable material. Incidentally, the cast or support 50 is intended for use with the hand and forearm, and is provided with a thumb hole 54. The double-knit material 52 of the cast 50 is compressed in the area or is formed with the area 56 much thinner than the remainder of the cast. In practice, the cast or support 50 may be activated with water and placed on the forearm with the thumb extending through the opening 54. The additional flap 56 has preferably been impregnated with water hardenable material, and after initial placement of the cast or support, the flap 56 is laid over the opposing edge of the blank and is smoothed down to achieve adequate and firm lamination with the remainder of the casting blank. The pressed down edges maintains the support's overall low profile after overlap and ensures that there are no irregularities on the inside of the support.

Figure 10:
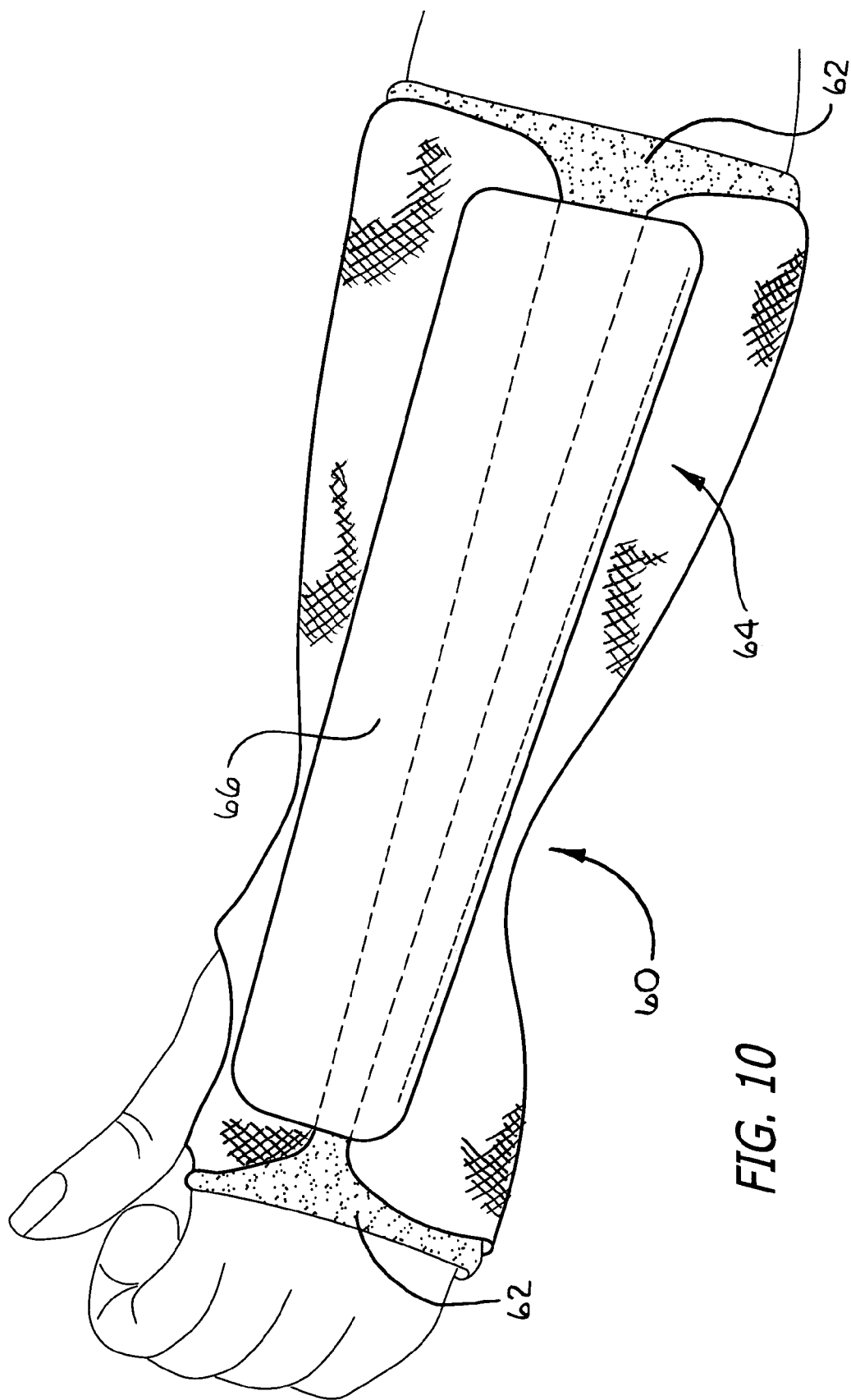
FIG. 10 is a perspective view of a support with the opposing edges being held together by a strip of impregnated fabric serving as the strapping system.

FIG. 10 shows one alternative configuration for securing a splint or support 60 in place. In FIG. 10 the hinge line is on the back side of the cast 60 so it is not visible. The cast 60 includes undercast padding 62, the casting blank 64 which may be formed of double-knit or spacer material, and an additional fabric strip 66 impregnated with water hardenable material. In practice, the casting blank 64 and strip 66 are initially activated, usually by water, the casting blank 64 is placed on the anatomy, and the strip 66 is placed over the edges of the casting blank 64, where it laminates to these edges to hold casting blank 64 firmly in place. When it is desired to open the cast, the medical personnel cuts through the strip 66 between the edges of blank 64 and the cast may be hinged open. The strip 66 is an alternative to the use of straps or Velcro® for holding a cast blank in place. Alternatively, the strip 66 may not be impregnated with resin and will still be able to overlap and laminate to the impregnated casting blank.

Figure 11:
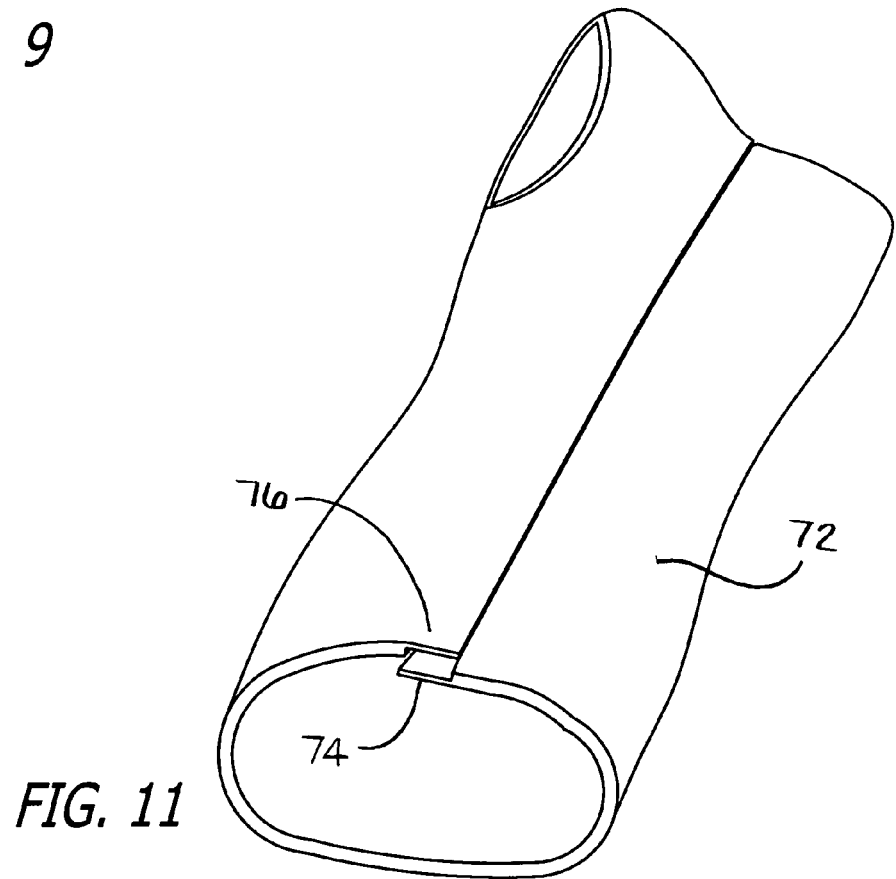
FIG. 11 is a perspective view showing the low profile benefits of compressing the edges of a blank in overlapping areas.

FIG. 11 shows a further embodiment of the invention in which the cast or support blank 72 is provided with edges 74, 76 which have been compressed, or which have been formed in a reduced thickness configuration. With the edges 74, 76 being impregnated along with the main portion of the blank 72, the edges of the double-knit or spacer type material will be firmly laminated together when applied, but with a smooth inner and outer configuration, to avoid irritation to the patient, which might otherwise be present where the edges overlap.

Figure 13:
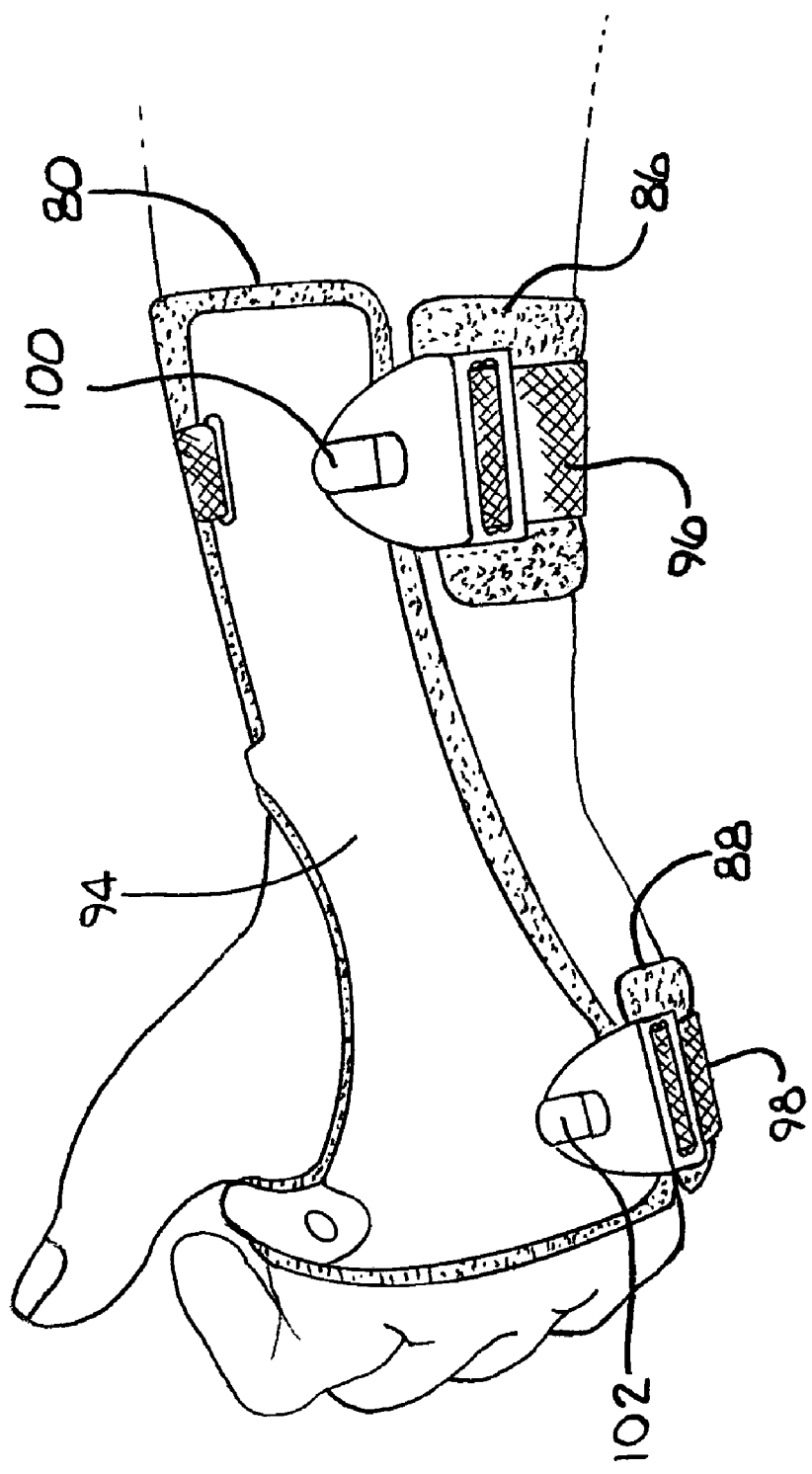
FIG. 13 is a schematic showing of the blank of FIG. 12 with an outer support member and straps for holding the brace or support onto the forearm of a patient.

Another embodiment is shown in FIGS. 12 and 13 of the drawings, with FIG. 12 showing the underlying hardenable material, and FIG. 13 showing the support mounted on the forearm of a patient.

In FIG. 12, the main body part 82 of the support or brace 80 may be made of double knit material, may be formed of several layers of fabric or may alternatively be a foam laminate, in each case impregnated with water hardenable material. The support 82 has a thumb hole 84 and two hardenable strap base support members 86 and 88. Hinge lines 90 and 92 of the type discussed hereinabove, are provided between the main body portion 82 of the support 80, and the strap support members 86 and 88 respectively.

FIG. 13 shows the support body 80 employed in an exoskeleton configuration, with the semiflexible plastic exoskeleton 94 overlying the water hardenable base 80 shown in FIG. 12. With regard to exoskeletal configurations, reference is made to U.S. Pat. Nos. 6,024,712 and 5,713,837, assigned to the assignee of the present invention, and the disclosures of which are hereby incorporated into this specification.

In the assembly of FIG. 13, the hardened base portion 80 is generally U-shaped, and the plastic exoskeleton 94 overlies the base portion 80 and includes flexible straps 96 and 98 which may be pivotally mounted to the body of the exoskeleton at hooks 100 and 102. The flexible straps 96 and 98 overly the hardened strap base support members 86 and 88. Straps 96 and 98 extend over and around the hardenable blank and interconnect the edges of the exoskeleton 94.

In practice, when it is desired to temporarily remove the entire brace or support, the straps 96 and 98 are released from hardened strap members 86 and 88, and the strap support members 86 and 88 are folded back along hinge lines 90 and 92, permitting full and easy removal of the brace.

Figure 14:
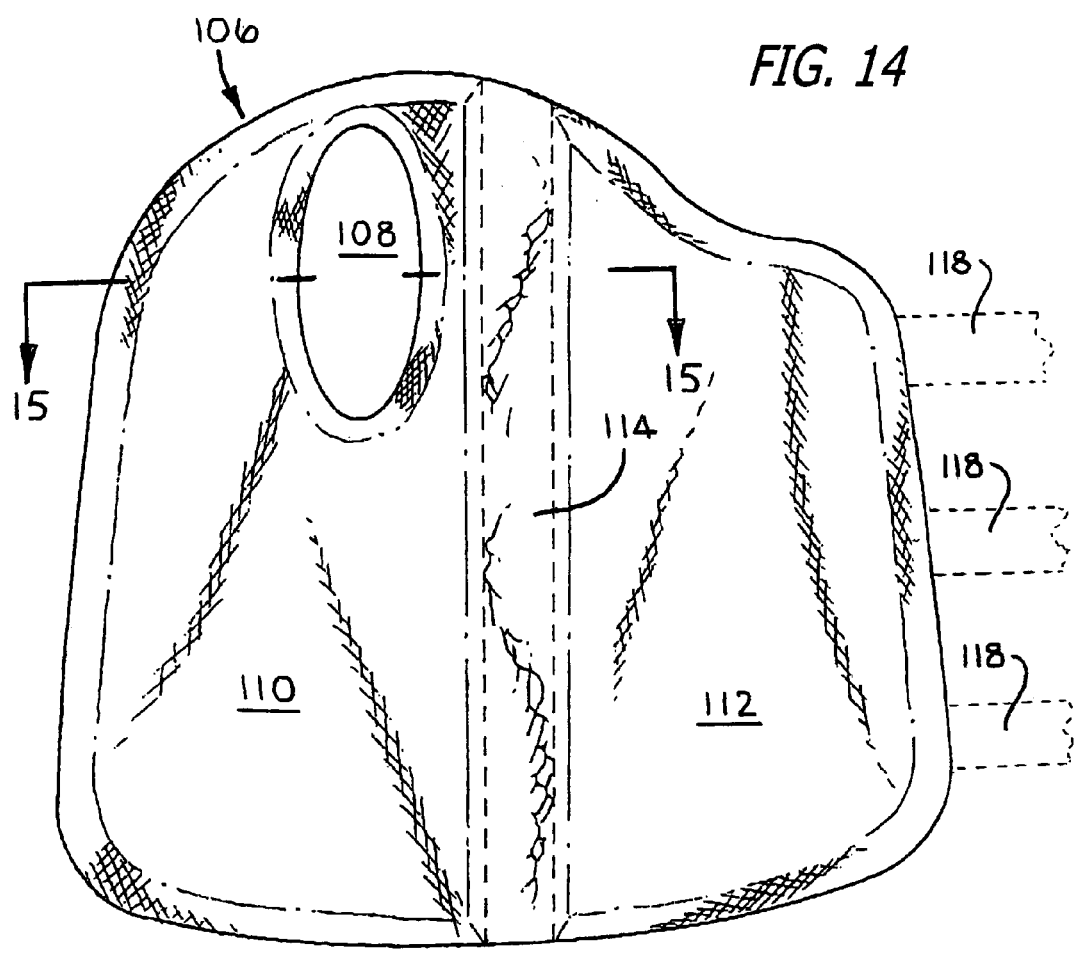
FIG. 14 shoes an alternative embodiment in which a broader hinge zone is employed.
Figure 15:
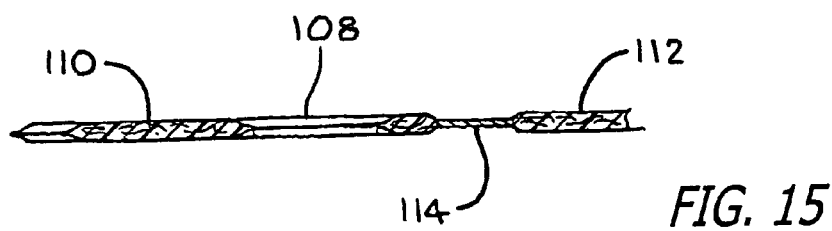
FIG. 15 is a cross-sectional view taken along the plane indicated by lines 15-15 of FIG. 14.

Referring now to FIG. 14 of the drawings, it shows a hardenable cast or support blank 106 including a thumb opening 108, and two sections 110 and 112 separated by a broad hinge zone 114, extending across the blank 106. In practice the blank may be formed of double knit material, or layers of fabric as discussed above; and the entire assembly may be impregnated with hardenable material, such as water hardenable urethane. As shown to advantage in FIG. 15, the broader hinge zone 114 is thinner than the rest of the blank, and contains less hardenable material. The thinner hinge zone 114 may be knit continuously with the sections 110 and 112, and with the knitting machine being programmed to form the thinner zone 114. Alternatively the thinner zone 114 may be compressed or stitched over its surface, so that it is relatively thin and will not absorb as much of the hardenable material as the sections 110 and 112. The blank 106 may be provided with straps 118 to hold the blank in place, as discussed hereinabove with other embodiments. If desired the blank 106 may be formed of several layers of high strength cloth or fabric, with the sections 110 and 112 being fairly loosely woven or knit and with the thinner section being compressed to a thinner configuration by stitching or by physical compression during the impregnation. The section 114 can also be made of a material with much less structural integrity to create the weakened zone, i.e., using spacer material with no high strength filaments in area 114 and spacer material with high strength filaments (such as glass filaments) in the remaining portions of the blank.

With the area 114 having relatively little hardenable material, and being of reduced thickness and strength, the cast may be hinged open along this zone, for inspection and washing of the enclosed portion of the anatomy, such as the forearm.

An edge treatment may be used in all embodiments where concurrent heat and pressure is used to reduce the thickness in these areas and, allow them to be somewhat bendable in comparison to the remaining portion of the bank when hardened. This type of "flex-edge" feature is created by reducing the thickness of the casting material, which serves to disrupt the structural integrity of the fabric, and reduces the amount of resin impregnation in this area. This same type of process can also be used to create a hinge at any point throughout the blank. The "flex-edge" feature will provide more comfort for the patient in areas typically very irritating. Reducing the thickness of the edges also serves to reduce the overall profile of the support in any overlapping areas. This feature is demonstrated in the devices of FIGS. 9 and 10.

The invention has been described with reference to casts or supports for immobilizing the forearm and the lower leg. There can be other configurations of casting blanks to provide immobilization to other portions of the body.

In accordance with one aspect of the invention, the support assembly may be comprised of a double-knit material with upper and lower knit or woven spaced apart layers with an inner matrix of woven or knit filaments or yarns. Instead of double-knit type material, other types of materials or laminates may be employed, in each case with at least one hinge line extending across the chosen material. The hinge line or zone has significantly less hardenable material along its extent, either as a result of compressing the laminate in this zone to a thickness significantly less than the remainder of the assembly, or by otherwise blocking the impregnation of hardenable material along the hinge zone. In the present specification and claims, when reference is made to "significantly less" hardenable material, or to a thickness which is "significantly less" than the remainder of the cast assembly, this means a reduction sufficient to permit hinging action. It is further noted that reducing the thickness of the laminate or the double-knit type material by engaging the upper and lower layers, or reducing the thickness significantly, alters the structural integrity of the material and allows bending of the cast along the hinge line.

In this regard, the fabric preferably includes a substantial portion of high strength fibers as disclosed in U.S. Pat. No. 6,186,966, to issue Feb. 13, 2001, assigned to the assignee of this application, and the subject matter of which is hereby incorporated into this specification by reference.

It is noted in passing that certain prior art hardenable orthopaedic splints and supports have employed many layers of fabric, for examples six or seven layers, and have employed stitching to preclude lateral shifting of the layers relative to one-another, but have not formed effective hinge lines by sufficiently reducing the hardenable material in the stitched areas.

Concerning another aspect of the construction of FIG. 1, the distance across the blank from left to right is somewhat greater than the transverse distance from the top to the bottom of the blank; and the hinge line advantageously extends in this shorter transverse direction. Similarly, when substantially rectangular cast or support blanks are used, the hinge line in some cases advantageously extends across the blank transverse to the longer dimension of the hardenable blank.

Although the hinges shown in the illustrations are shown to be relatively longitudinal to the cast, there can be situations where the hinge is otherwise relatively angled to the cast. In some cases, the hinge can be transverse to the support. Likewise, there can be situations where there is more than one hinge and the relative relationships can be at an appropriate angle relative to each other. As appropriate, suitable padding material may be provided between the support and the bodily part. Although sewing has been described as one preferred method for creating the hinge, there can be other suitable techniques for creating flexibility in the blank to form the hinge construction. When spacer or double-knit type material is employed, the two outer layers may be drawn together to form a hinge line by stitching, by heat welding of the outer layers together when they include plastic material, by adhesive, or by any other desired technique. Alternatively, a narrow band of the double-knit material could be protected or clamped together during urethane impregnation, to avoid impregnation and subsequent hardening of the band, which is to form the hinge. As a further alternative, the reduced thickness hinge line or strip may be integrally knit into the double-knit material as the material is initially formed or knit. It is also noted that, instead of using water-hardenable material, other hardenable combinations of materials may be employed as hardening agents. Accordingly, the invention is not limited to the specific embodiments as shown in the drawings and as described in detail hereinabove.

What is claimed is:

1. A versatile hardenable cast or support comprising:
   double-knit material formed to conform to a portion of the anatomy;
   said double-knit material being formed of an upper layer of woven or knit material, and a lower layer of woven or knit material spaced from said upper layer by a predetermined distance, with a matrix of filaments extending between said layers, said filaments being integrally woven or knitted into both said upper and lower layers;

hardenable material impregnated into said double-knit type material across its entirety;

at least one V-shaped hinge line extending substantially across said double-knit material wherein the double-knit material is compressed along the hinge line so that said hinge line is of significantly reduced thickness relative to the remainder of said double-knit type material and there is less hardenable material along the hinge line than in the remainder of the double-knit material;

whereby said cast or support may be folded open along said hinge line.

2. A cast or support as defined in claim 1 for limiting movement of at least part of the arm.

3. A cast or support as defined in claim 1 for limiting movement of at least part of the leg.

4. A cast or support as defined in claim 1 wherein said hardenable material is a water-hardenable urethane.

5. A cast or support as claimed in claim 1 including releasable straps for securing the cast about the human anatomy.

6. A cast or support as claimed in claim 1 wherein the hinge is formed by compression of the double-knit material along the hinge line.

7. A cast or support as defined in claim 6 wherein said hinge line is created by heat.

8. A cast or support as claimed in claim 6 wherein the hinge line is created by a sew line.

9. A cast or support as defined in claim 1 wherein said hinge line is integrally knit into said double-knit material.

10. An orthopaedic cast or support comprising:

a blank formed of a fabric for application to the anatomy of a patient, said fabric being impregnated with hardenable material across its entirety; and at least one V-shaped hinge line extending substantially across the fabric, the blank is compressed along the hinge line so that said hinge line is of significantly reduced thickness relative to the remainder of the blank;

wherein said blank is a continuous fabric but with a significantly lesser amount of said hardenable material located along said hinge line as compared with elsewhere in the blank;

whereby the cast or support may be folded open along the hinge line.

11. An orthopaedic cast or support as defined in claim 10 wherein said fabric is a high strength fabric.

12. A cast or support as claimed in claim 10 including releasable straps for securing the cast or support about the human anatomy.

13. A cast or support as claimed in claim 10 wherein the hinge is formed by a zone of relatively thinner material, and wherein the thinning is formed by compression of the impregnated material along the hinge.

14. A cast or support as claimed in claim 13 wherein the hinge is created by a sew line, the sewing being effective to form the hinge.

15. A cast or support as defined in claim 10 wherein said hinge is integrally formed in the original fabrication of said material.

16. An orthopaedic cast or support as defined in claim 10 wherein at least one hardenable strap member extends outwardly from said blank, and wherein said hinge line extends across the base of said strap member adjacent the junction between the strap member and the blank.

17. An orthopaedic cast or support as defined in claim 10 wherein an exoskeleton is provided to extend over said blank and give additional support when said blank is applied to a patient.

18. A versatile hardenable cast or support comprising:

double-knit material formed to conform to a portion of the anatomy;

the double-knit material being formed of an upper layer of woven or knit material, and a lower layer of woven or knit material spaced from the upper layer by a predetermined distance, with a matrix of filaments extending between the layers, the filaments being integrally woven or knitted into both the upper and lower layers;

hardenable material impregnated into the double-knit material across its entirety;

at least one V-shaped hinge line extending substantially across the double-knit material such that the double-knit material is compressed along the hinge line; and wherein the hinge line is of significantly reduced thickness relative to the remainder of the double-knit material and there is less hardenable material along the hinge line than in the remainder of the double-knit material;

wherein the cast or support may be folded open along the hinge line;

wherein the knitted material has a hole for a thumb to protrude from one side of the material to the other side of the material.

* * * * *